(12) United States Patent
Martikka et al.

(10) Patent No.: US 11,457,865 B2
(45) Date of Patent: Oct. 4, 2022

(54) WEARABLE SPORTS MONITORING EQUIPMENT FOR MEASURING HEART RATE OR MUSCULAR ACTIVITY AND RELATING METHOD

(71) Applicant: Suunto Oy, Vantaa (FI)

(72) Inventors: Mikko Martikka, Vantaa (FI); Heikki Nieminen, Vantaa (FI); Kimmo Pernu, Vantaa (FI); Olli-Pekka Ojanen, Vantaa (FI); Erik Lindman, Vantaa (FI)

(73) Assignee: Suunto Oy, Vantaa (FI)

( * ) Notice: Subject to any disclaimer, the term of this patent is extended or adjusted under 35 U.S.C. 154(b) by 0 days.

(21) Appl. No.: 14/943,049

(22) Filed: Nov. 17, 2015

(65) Prior Publication Data
US 2016/0143592 A1 May 26, 2016

(30) Foreign Application Priority Data

Nov. 19, 2014 (FI) ...................................... 20146010
Nov. 19, 2014 (GB) ...................................... 1420545

(51) Int. Cl.
*A61B 5/00* (2006.01)
*A61B 5/0205* (2006.01)
(Continued)

(52) U.S. Cl.
CPC .......... *A61B 5/6801* (2013.01); *A61B 5/0006* (2013.01); *A61B 5/0205* (2013.01);
(Continued)

(58) Field of Classification Search
None
See application file for complete search history.

(56) References Cited

U.S. PATENT DOCUMENTS 3,542,013 A * 11/1970 Stephenson .......... A61B 5/0428
600/508
5,025,791 A 6/1991 Niwa
(Continued)

FOREIGN PATENT DOCUMENTS

EP        0659384 A1    6/1995
EP        0875199 A1   11/1998
(Continued)

OTHER PUBLICATIONS

Xu, D. et al; "Reduced heart rate variability during sleep in long-duration spaceflight"; Am J Physiol Regul Integr Comp Physiol 305: R164-R170, 2013.*

(Continued)

*Primary Examiner* — Lori A. Clow
*Assistant Examiner* — Marie Archer
(74) *Attorney, Agent, or Firm* — Laine IP Oy (57) ABSTRACT

The invention relates to wearable electronic equipment and method for measuring heart rate or muscular activity of a person. The equipment comprises one or more heartbeat or muscular activity sensors for providing a heartbeat or muscular activity signal, respectively, and a motion sensor for providing a motion signal corresponding to movement of the person. In addition, there are provided processing means for detecting from the heartbeat or muscular activity signal first events corresponding to individual heartbeats or muscle activations, respectively, and from the motion signal second events corresponding to movement changes stronger than a predefined threshold. The processing means are further programmed to form a first time series of said first events, and to determine the heartbeat or muscular activity parameter using the first time series. According to the invention, the processing means are programmed to omit from said first time series those first events that coincide with and/or take (Continued)

place at the same frequency as the second events. The invention helps to remove motion-induced artifacts from ECG and EMG signals for more accurate sports performance monitoring and characterization.

19 Claims, 10 Drawing Sheets

(51) Int. Cl.
    *A61B 5/11*     (2006.01)
    *A61B 5/0245*     (2006.01)
    *A61B 5/25*     (2021.01)
    *A61B 5/296*     (2021.01)
    *A61B 5/389*     (2021.01)

(52) U.S. Cl.
    CPC .............. *A61B 5/0245* (2013.01); *A61B 5/11* (2013.01); *A61B 5/25* (2021.01); *A61B 5/296* (2021.01); *A61B 5/389* (2021.01); *A61B 5/721* (2013.01); *A61B 5/7282* (2013.01); *A61B 5/7285* (2013.01); *A61B 5/6804* (2013.01); *A61B 5/6831* (2013.01); *A61B 5/725* (2013.01); *A61B 5/7257* (2013.01)

(56) References Cited

U.S. PATENT DOCUMENTS

| | | | | |
|---|---|---|---|---|
| 6,002,957 | A * | 12/1999 | Finneran | A61B 5/0492 600/382 |
| 6,937,900 | B1 * | 8/2005 | Pianca | A61N 1/36542 607/18 |
| 2004/0034285 | A1 * | 2/2004 | Sahashi | A61B 5/0245 600/300 |
| 2004/0034294 | A1 * | 2/2004 | Kimball | A61B 5/14552 600/323 |
| 2006/0031102 | A1 * | 2/2006 | Teller | A61B 5/411 705/3 |
| 2007/0285868 | A1 * | 12/2007 | Lindberg | A61B 5/0245 600/382 |
| 2010/0198087 | A1 | 8/2010 | Takahashi et al. | |
| 2012/0123232 | A1 * | 5/2012 | Najarian | A61B 5/0022 600/345 |
| 2014/0275854 | A1 * | 9/2014 | Venkatraman | A61B 5/721 600/301 |
| 2015/0065896 | A1 * | 3/2015 | Takahashi | A61B 5/721 600/500 |
| 2016/0051158 | A1 * | 2/2016 | Silva | A61B 5/721 600/479 |
| 2016/0058386 | A1 * | 3/2016 | Wang | A61B 5/721 600/509 |
| 2016/0228066 | A1 * | 8/2016 | Szabados | A61B 5/01 |
| 2016/0249864 | A1 * | 9/2016 | Kang | A61B 5/02438 340/870.07 |
| 2017/0095159 | A1 * | 4/2017 | Bonomi | A61B 5/024 |

FOREIGN PATENT DOCUMENTS

| | | |
|---|---|---|
| EP | 1297784 A1 | 4/2003 |
| WO | WO 2010077997 | * 12/2009 |

OTHER PUBLICATIONS

Douglas L. Jones, The DFT, FFT, and Practical Spectral Analysis. OpenStax CNX. Feb. 24, 2007 http://cnx.org/contents/d2c6d393-3590-403d-8a18-c892055b046b@2.2.*

Keselbrener, L. et al; "Selective Discrete Fourier Transform Algorithm for Time-Frequency Analysis: Methods and Application on Simulated and Cardiovascular Signals"; IEEE Transactions on Biomedical Engineering; vol. 43; No. 8; Aug. 1996; p. 789-802.*

Asada, H. et al; "Active Noise Cancellation Using MEMS Accelerometers for Motion-Tolerant Wearable Bio-sensors"; Proceedings of the 26th Annual International Conference of the IEEE EMBS; San Francisco, CA, USA, Sep. 1-5, 2004; p. 2157-2160. (Year: 2004).*

Yasin, M-F. et al; "Measurement of noise characteristics of MEME accelerometers"; Solid-State Electronics 47 (2003) 357-360 (Year: 2003).*

Pantelopoulos, A., & Bourbakis, N. G. (2009). A survey on wearable sensor-based systems for health monitoring and prognosis. IEEE Transactions on Systems, Man, and Cybernetics, Part C (Applications and Reviews), 40(1), 1-12. (Year: 2009).*

Lopez-Silva, S. M., et al; "Heuristic algorithm for photoplethysmographic heart rate tracking during maximal exercise test" (2012), Journal of Medical and Biological Engineering, 32(3), 181-188 (Year: 2012).*

Pandia K. et al: Motion Artifact cancellation to obtain heart sounds from a single chest-worn accelerometer. Conference Proceeding Article of the IEEE International Conference on Acoustics, Speech and Signal Processing. pp. 590-593. Mar. 14, 2010.

Renevey P. et al: Wrist-located pulse detection using ir signals, activity and nonlinear artifact cancellation.Conference Proceedings Article of the IEEE Engineering in Medicine and Biology Society. p. 3030-3033, Oct. 25, 2001.

Sweeney K.T. et al: Artifact Removal in Physiological Signals Practices and Possibilities. IEEE Transactions on Information Technology in Biomedicine. vol. 16, p. 488-500. May 1, 2012.

* cited by examiner

WEARABLE SPORTS MONITORING EQUIPMENT FOR MEASURING HEART RATE OR MUSCULAR ACTIVITY AND RELATING METHOD

FIELD OF THE INVENTION

The invention relates to a wearable electronic devices and systems for monitoring sports performances. In particular, the invention relates to an improved solution for determining heart rate or muscular activity of a person during a performance using electrocardiographic (ECG) or electromyographic (EMG) measurements during a performance.

BACKGROUND OF THE INVENTION

Heart rate sensors are commonly used for monitoring and characterizing sports performances. Most commonly, they are based on electric measurement of heart activity using electrodes placed on the skin of a person, i.e. using an ECG measurement. Heart rate can be determined by detecting individual heartbeats from the ECG signal and counting their frequency. Heart rate as such is an important characteristic parameter of the performance but it can also be used to estimate for example energy consumption of the person. This is also very common in existing sports monitoring devices and systems.

There are devices, which contain both a heartbeat or muscular activity sensor and an acceleration sensor. For example, in US 2005/0177059, an acceleration sensor is used for improving the accuracy of estimation of energy consumption or determination of pace of running by simultaneous measurement of muscular activity and acceleration. In one embodiment, the moment of foot coming off the ground is determined using the acceleration sensor.

Heart rate sensors are sensitive not only to the actual heartbeat signal but also noise and fluctuations coming from other sources. One source of error is that the contact impedance between the measurement electrodes and skin varies depending on the quality of contact, which can vary during an exercise due to stepping or other movements during the performance. Another source of error comprises electric potential changes on the surface of the skin or at the measurement equipment due to other sources than heart activity. For example, if static electricity is accumulated close to the contact area of the measurement electrodes or at the material of the heart rate measurement device itself, it may be seen as an artifact in the signal measured. Such accumulation may occur for example if the clothes of the person rub against the measurement equipment due to stepping or other movements. The abovementioned errors are emphasized if the input impedance of the measurement electronics is not infinite (as would usually be in an ideal case) but relatively low, as the case typically is with electronic measurement equipment. Both errors are also more likely to take place in the beginning of a performance when the skin, contacts and clothes are typically dry.

Similar problems are encountered with muscular activity EMG measurements, which often have even lower signal levels and are therefore prone to influence of measurement artifacts of the abovementioned kinds.

U.S. Pat. No. 7,797,039 discloses one method for recognizing and measuring heartbeat in physical training using sensors integrated into an outfit of a person. The method comprises measuring the ECG signal at the waist or level below the waist using wearable sensors. The accuracy of the method is improved by processing and examining signals received from the heart with to or more different ways, which improved reliability of calculation and decreases the impact of noises. For example, the same ECG signal may be conducted to two different channels in which different signal filters are used and then the filtered signals are summed to reduce noise. In another example, two different but simultaneous ECG signals are used. In still another example, an ECG signal and movement signal are collected simultaneously and used to reduce muscle and movement induced noise in different channels. The intention is to filter out the contribution of signals coming from muscle activity or passive muscle shaking, which contribution may be strong compared with ECG signals, because the whole measurement is carried out at the waist level or below that, i.e. relatively far from the heart. The method requires simultaneous measurement of both ECG and EMG signals or the ECG signal at several different locations and is suitable for improving data quality in situations where the ECG and EMG sensors stay in place and in reliable contact with skin all the time, which can indeed be the case when tight outfit with integrated sensors is used. The method is, however, relatively computation-intensive and requires therefore a lot of processor and battery power.

There are no powerful methods known that would specifically address the abovementioned problems relating to undesired effects of varying impedance between the measurement electrodes and skin or electric potential changes on the surface of the skin or at the measurement equipment. In particular, there are no computationally lightweight method that would allow improving heartbeat or muscular activity measurements essentially real-time.

Thus, there is a need for improved heartbeat and muscular activity measurement solutions.

SUMMARY OF THE INVENTION

It is an aim of the invention to provide a novel measurement device or system that mitigates the undesired effects of at least some sources of error in real-time sports performance monitoring. It is also an aim to provide a novel method for this purpose.

The invention is based on the observation that often the most prominent sources of error are related to rhythmic movements of the person being monitored. In particular, static electricity is generated due to friction between the skin and/or heart rate or muscle activity measurement equipment and clothes of the user that move according to the rhythm of the performance, such as gait in running or walking. The accumulated charge causes potential changes in the vicinity of the measurement electrodes or is directly discharged to the measurement electronics, causing a distortion in the signal. Also the contact pressure and/or area thus contact impedance between the electrodes typically varies according to the same rhythm. To mitigate these sources of error, the invention utilizes individual heartbeat or muscle activity event-based measurement combined with data obtained from a motion sensor positioned so as to reflect movement of the person and therefore also the movement of the heartbeat or muscle activity sensor carried by the person.

The invention thus provides wearable electronic equipment for measuring heart rate or muscular activity of a person, the equipment comprising at least one heartbeat or muscular activity sensor, such as an electronic electrocardiographic (ECG) or electromyographic (EMG) sensor, for providing a heartbeat or muscular activity signal and processing means for deriving heartbeat data or muscular activity data from the heartbeat or muscular activity signal.

In addition, there are provided processing means for detecting from the heartbeat or muscular activity signal first events corresponding to individual heartbeats or muscle activations, respectively, and from the motion signal second events corresponding to movement changes stronger than a pre-defined threshold. In other words, the processing means are able to trigger events based on the raw signals, if predefined characteristic features, such as R-peaks in a heartbeat signal or high accelerations in the motion signal, are found. The processing means are further programmed to form a first time series of said first events (the series thus forming form a "first event signal"), and to determine the heartbeat or muscular activity parameter using the first time series. In addition, the processing means are programmed to omit from said first time series those first events that coincide with and/or take place at the same frequency as the second events. In other words, the processing means is programmed to include in the first time series such first events that are asynchronous, i.e., take place at different points of time, and/or take place at a different frequency than the second events. Two basic embodiments for carrying out this selective process, i.e. event triggering prevention and common-frequency filtering, are discussed in detail later.

The invention also provides a corresponding method.

More specifically, the invention is characterized by what is stated in the independent claims.

The invention provides considerable advantages. Most notably, the invention solves the problem of generation of movement-induced repeating errors in a heartbeat signal. The heartbeat or muscular activity signal may contain a contribution by changing contact impedance between the measurement electrodes and the skin of the person due to the movement of the measurement device. The term contact impedance should be understood broadly, depending on the measurement technique (e.g. electrical impedance in the case of electrical measurement, optical impedance in the case of optical measurement and mechanical impedance in the case of mechanical measurement). Alternatively or in addition to that, in particular in the case of electrical measurement, the signal may contain a contribution by potential changes in the vicinity of the measurement device due to accumulation of static electricity, for example due to friction between the measurement device and clothes of the person. The invention is effective against both types of errors in the signal, these errors typically has the largest undesired effect on the monitoring and provides an elegant and powerful solution for removing this effect. In particular at the beginning of an exercise, when the measurement electrodes of the measurement device and also the skin are dry and both the contacting problem and static electricity phenomena referred to above are significantly present. When there is more sweat present, the situation typically stabilizes and error signal decreases as the contact impedance decreases and static electricity is not accumulates since electric potential differences are evened out as the clothing, measurement equipment and skin become "grounded".

The invention is applicable in particular for electronic heartbeat muscle activity monitoring but can be used also in connection with other measurements techniques, since many, if not all, of them are sensitive to the same or similar kinds of motion artifacts.

As concerns muscular activity measurements, the invention is most effective when measuring repeating, relatively constant-frequency activity, such as cadence-related or other activation sequences of muscles.

The dependent claims are directed to selected embodiments of the invention.

There are two principal embodiments for carrying out said omitting of first events. In the first one, the equipment is configured to disregard periods of the heartbeat or muscular activity signal that coincide with the second events (e.g. high acceleration events) when forming said first time series. Thus, even if a first event would be detected during a second event, it will not be represented in the first time series of events. Alternatively the whole detection can be "switched off" during those periods. As a result, the first event signal comprises a (potentially) incomplete collection of heartbeat or muscle activity events. There is, however, enough data to derive for example the heart rate reliably. To "complete" the first event signal, the processing means can be further programmed to perform a Discrete Fourier Transform (DFT) of the first time series and to determine said heartbeat or muscular activity parameter using the output of the DFT. The transformed signal will reveal the true frequency of events even though some of them would have been disregarded because of too high simultaneous acceleration, because the DFT sees a longer time span of events.

The second principal embodiment comprises the processing means being programmed to form a second time series of the second events detected (i.e., to form a "second event signal") and removing frequency components of the first time series ("first event signal") that are common with at least one frequency component of the second time series. This common-frequency filtering embodiment requires more computation than the event triggering-preventing embodiment described above but ensures that constant-frequency motion-based artifacts do not affect the measurement result.

Although working well also as such, the event triggering-preventing method and common-frequency filtering methods can also be used in parallel or successively so as to minimize the possibility of false events being recorded.

The processing means may be programmed to carry out the removing by performing a Discrete Fourier Transform (DFT) of the first time series, performing a Discrete Fourier Transform (DFT) of the second time series, and reducing common frequency components of the first and second time series from the first time series.

In both embodiments, the first (and/or second) time series is(/are) preferably formed as binary series where one bit value represents detected events and the other bit value non-existence of such occurrence. For such binary series, the DFT computation operations are extremely efficient.

The data to be derived may comprise e.g. heart rate, heartbeat interval, energy consumption, or muscle activation rate, strengths or timings, or any other quantity derivable from the heartbeat or muscle activation signal.

The invention can be used also in connection with other sensor types than electronic ECG/EMG sensors.

According to one embodiment, the method of the invention comprises measuring a heartbeat or muscular activity signal using a measurement device with a sensor head positionable against the skin of the person (and therefore being susceptible to motion artifacts) and deriving at least one parameter depicting heartbeat or muscular activity from the heart or muscular activity signal. Movement of at least one part of the measurement device is simultaneously measured using an acceleration sensor for providing a motion signal. Before deriving the at least one parameter depicting heartbeat or muscular activity, the heartbeat or muscular activity data is processed so as to form a time series of heartbeat or muscular activity events so that those heartbeat or muscular activity events that coincide with and/or take place at the same frequency as strong acceleration events, are omitted, i.e. not being marked as events in the time series.

Preferably, the heartbeat or muscular activity sensor and the motion sensor are located in the same device unit, such as a heart rate belt or smart garment. This ensures that the motion signal corresponds to actual movement of the heartbeat or muscular activity sensor. It is however possible that the sensors are located in different device units potentially located on different body parts, because their rhythmic movements are typically not independent and therefore sufficient information for removing rhythmic artifacts can be obtained.

The processing means may comprise a processing unit located in a single device unit or two or more separate processing units of different device units, depending on the overall equipment architecture. Examples of architecture include a single device unit being a heart rate measurement module that is part of or is attachable to a garment, or a wrist-worn unit comprising integrated sensors, or a distributed device model having two or more device units in wireless communication link with each other.

The processing unit(s) referred herein and contained in the one or more device units may comprise a data processor of any kind, in particular a microcontroller or a microprocessor together with potentially required related components, such as memory components (e.g. RAM, ROM) and input/output circuits functionally connected thereto. In the distributed device model, two or more processing units located in two or more device units and programmed to carry out different parts of the present method together form the processing means.

According to one embodiment, the same device unit where at least one of the sensors, preferably both sensors, is contained in, also comprises the at least part of the processing means, in particular a signal analysis unit capable of making the necessary detection of characteristic features, i.e., feature indicative of heartbeat events, muscle activation events and/or high acceleration events. This device unit can in particular be a heart rate belt or smart shirt or a removable computing and communication unit designed therefor. Particularly preferred is the inclusion of at least the event-detection part of the processing means to the same device unit which contains or is attachable to ECG or EMG sensors. To allow for cleaning of motion-induced artifacts from the signal at the measurement site, also the part of the processing means capable of omitting ECG or EMG events that take place during high acceleration and/or at the same frequency as the acceleration events can be included in the same device unit.

According to one embodiment, the wearable electronic equipment comprises a pair of ECG electrodes positionable against the chest of the person for providing the ECG signal, typically laminated within a fabric structure.

According to one embodiment, the ECG or EMG electrodes are connected to a measurement electronics having an input impedance less than 50 kOhm, in particular less than 25 kOhm. Such solutions are popular and suitable for heartbeat detection but suffer from influences of outside sources of error, which the present invention, however, mitigates.

According to alternative embodiments, the heartbeat sensor comprises an optical sensor, a pressure sensor or an acceleration sensor. Thus, instead of electrically detectable cardiographic response, the sensor may be sensitive for example to optically detectable cardiovascular changes due to heartbeats, cardiovascular pressure changes due to heartbeats or cardiovascular-induced motion detectable on the surface of skin.

The location of the heartbeat sensor during the performance may be chest, waist, neck, wrist, upper arm or auricle, to mention some examples.

According to one embodiment, the motion sensor comprises an acceleration sensor providing an acceleration signal as the motion signal.

According to one embodiment, the device containing the heartbeat or muscular activity sensor is provided with a communication unit for communicating the heart rate or muscular activity data to another device containing at least part of the processing means. The acceleration can be measured in either of the devices.

According to one embodiment, the heartbeat or muscular activity signal measurement, movement measurement, and signal processing steps are all carried out in a heart rate belt or muscular activity belt, or in a heart rate measurement module attachable to a heart rate belt or to a smart garment having a mounting zone for such a module.

In a distributed model, the heartbeat or muscular activity signal measurement steps are carried out in a heart rate belt, smart garment or heart rate measurement module attachable to a heart rate belt or a smart garment with a mounting zone for such module, and at least part of signal processing is carried out in another device wirelessly communicating with the heart rate belt or heart rate measurement module.

Definitions

The term "wearable equipment" covers all mobile devices and multi-device systems, which are designed or can otherwise to be attached to one or more body parts directly or via a piece of clothing, including various kinds of shirts, jackets, pants and shoes, for example, or wearable accessory, such as an arm holder for a wearable mobile phone. Single wearable devices include in particular wrist-worn computers, mobile phones, heart rate belts, smart garments and sensor units of various kinds, such as ECG and EMG measurement modules, satellite positioning units, acceleration measurement units (foot and arm "pods"), providing some or all of the functionalities as herein described. In other words, the invention covers individual self-contained units providing the necessary functionalities of the invention and as well as systems formed of a plurality of separate units capable of communicating with each other so as to form an operational entity providing said functionalities.

Unless otherwise mentioned, references to a "heart rate belt" and "smart garment" include the option that the belt or garment contains, in addition to an integral heartbeat sensor, an integral computing and communication unit (hereinafter: processing unit) and the option that the computing and communication unit is mountable to the belt or garment as a releasable module in functional connection with the heartbeat sensor. The other way round, the term "module" may equally refer to an integral module in a heart rate belt or smart garment or a removable module functionally connectable with a belt or garment.

The term "R-peak" refers to the middlemost wave of the so-called QRS complex formed by three graphical deflections seen on a typical electrocardiogram caused by depolarization of the right and left ventricles of the human heart. The concept of R-peak, as well as algorithms for detection thereof, is known to those skilled in the art and publicly available.

Next, embodiments and advantages of the invention are described in more detail with reference to the attached drawings.

DETAILED DESCRIPTION OF EMBODIMENTS

Figure 1A:
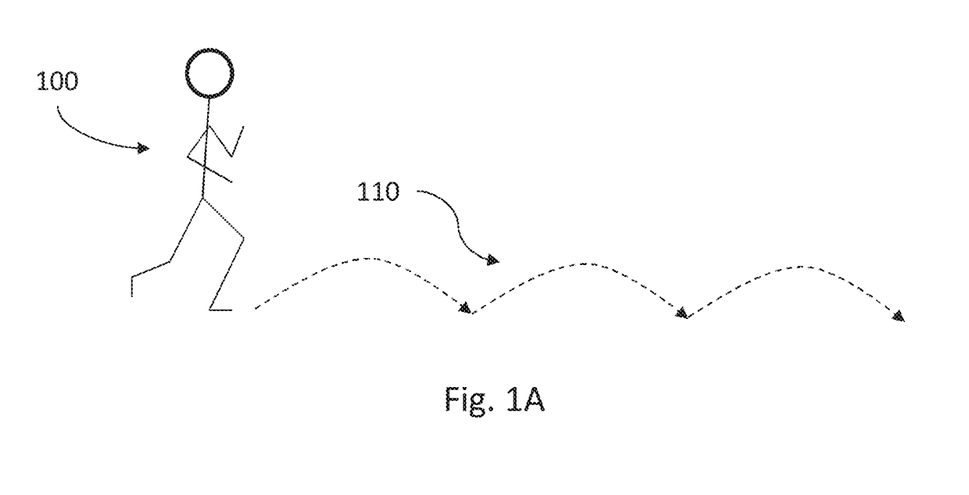
FIG. 1A illustrates a runner taking rhythmic steps.
Figure 1B:
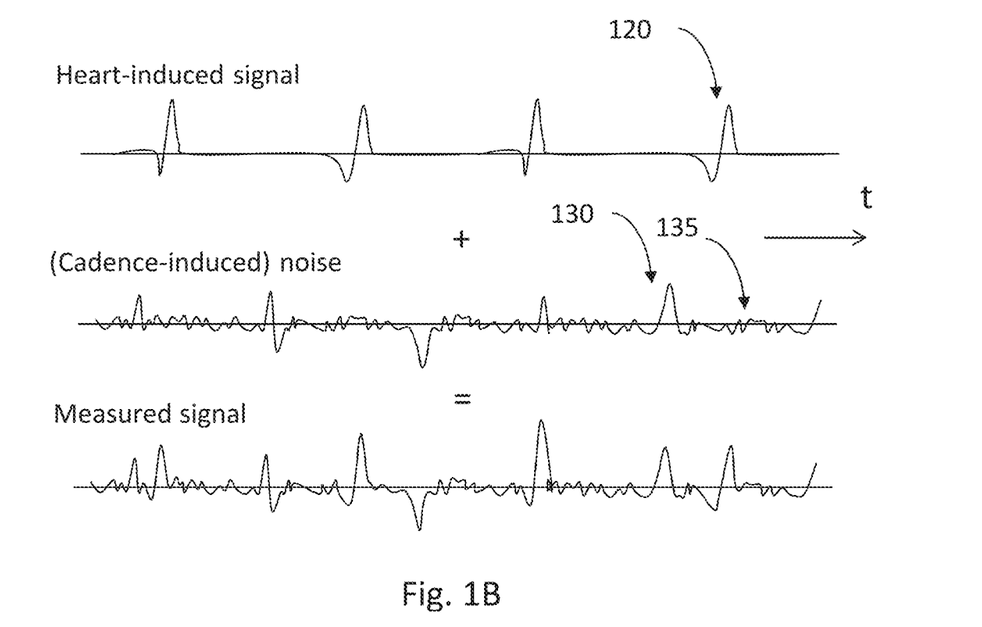
FIG. 1B shows schematic graph of the formation of a measured ECG signal by heartbeat-induced signal and cadence-influenced noise.

FIG. 1A illustrates one preferred field of use of the invention, i.e. running, and FIG. 1B shows related ECG signal formation. In an ideal case, the heartbeat of the runner 100 produces a clean ECG signal with easily detectable heartbeat waveforms 120 as illustrated by the uppermost graph of FIG. 1B. However, in practice, there is always random noise 135 present, as well as systematic noise, i.e., artifacts 130 induced by the movement 110 of the runner 100. In the case of rhythmic cadence, the artifacts are typically repeated periodically, following the more or less constant rhythm of the movement. The random noise 135 and artifacts 130 are illustrated by the middle graph of FIG. 1B. Thus, the real measured signal contains the sum of the real heartbeat signal and the noise and artifact signals, which is illustrated by the lowermost graph of FIG. 1B. From this sum signal, it is much more difficult to detect the heartbeats robustly than from the ideal ECG signal.

Figure 1C:
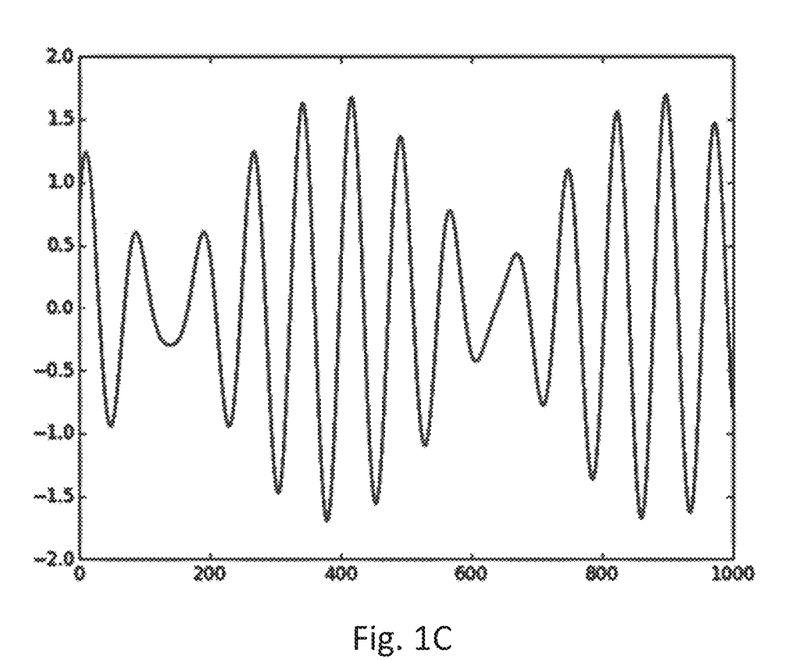
FIG. 1C depicts as a graph a combined signal of two different frequencies in time domain.
Figure 1D:
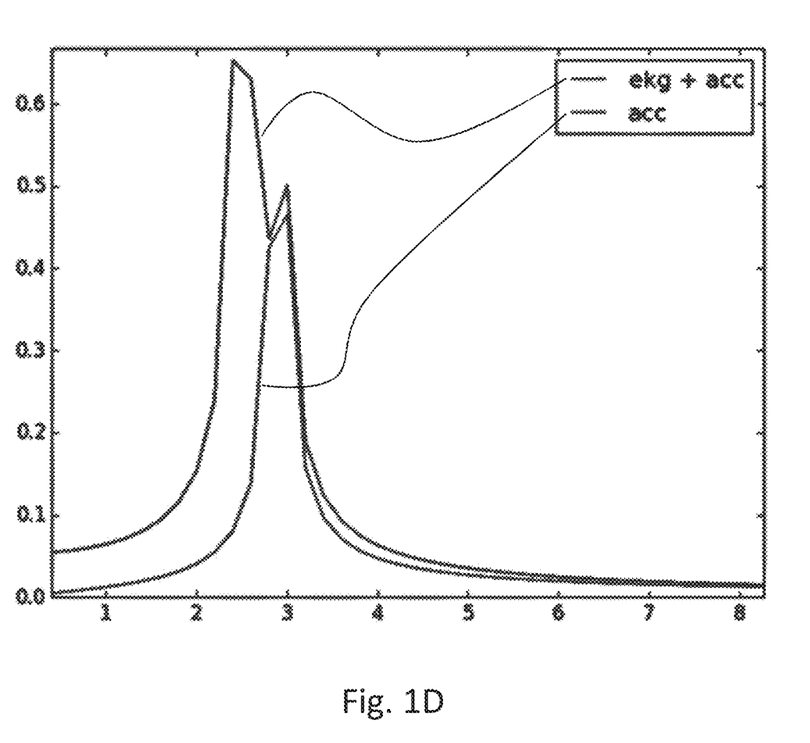
FIG. 1D shows the amplitude response of the Fourier transformation of the combined signal of FIG. 1C and one of the signals separately.

FIGS. 1C and 1D illustrate the problem in more detail using a theoretical example. FIG. 1C comprises a signal which is generated by summing two oscillating signals having different frequencies, say an artificial acceleration signal and artificial heartbeat signal. The upper curve of FIG. 1D shows a Fourier transformation of the signal of FIG. 1C, that is, the combined amplitude of frequency components of the artificial acceleration and heartbeat signals. It can be seen that there are two peaks close to each other, but one cannot say which one of the peaks is due to heartbeat and which one due to acceleration. The lower curve of FIG. 1D shows the Fourier transformation of the acceleration signal alone. It can be seen that the second peak of the combined amplitude corresponds to the acceleration peak, whereby the first peak must be the heartbeat peak. Mathematically speaking, a simple subtraction of the acceleration peak from the combined peak brings up the heartbeat peak alone. As this is, however, computation intensive to do for raw signals, the method is herein describes an event triggering-based method yielding essentially the same result with much lower computational power needed. Alternatively, ignoring potentially motion-influenced peaks and using statistical deduction, again in the event space, can be used to determine the heart rate as also explained later in more detail. First, exemplary equipment architecture models are presented.

Figure 2A:
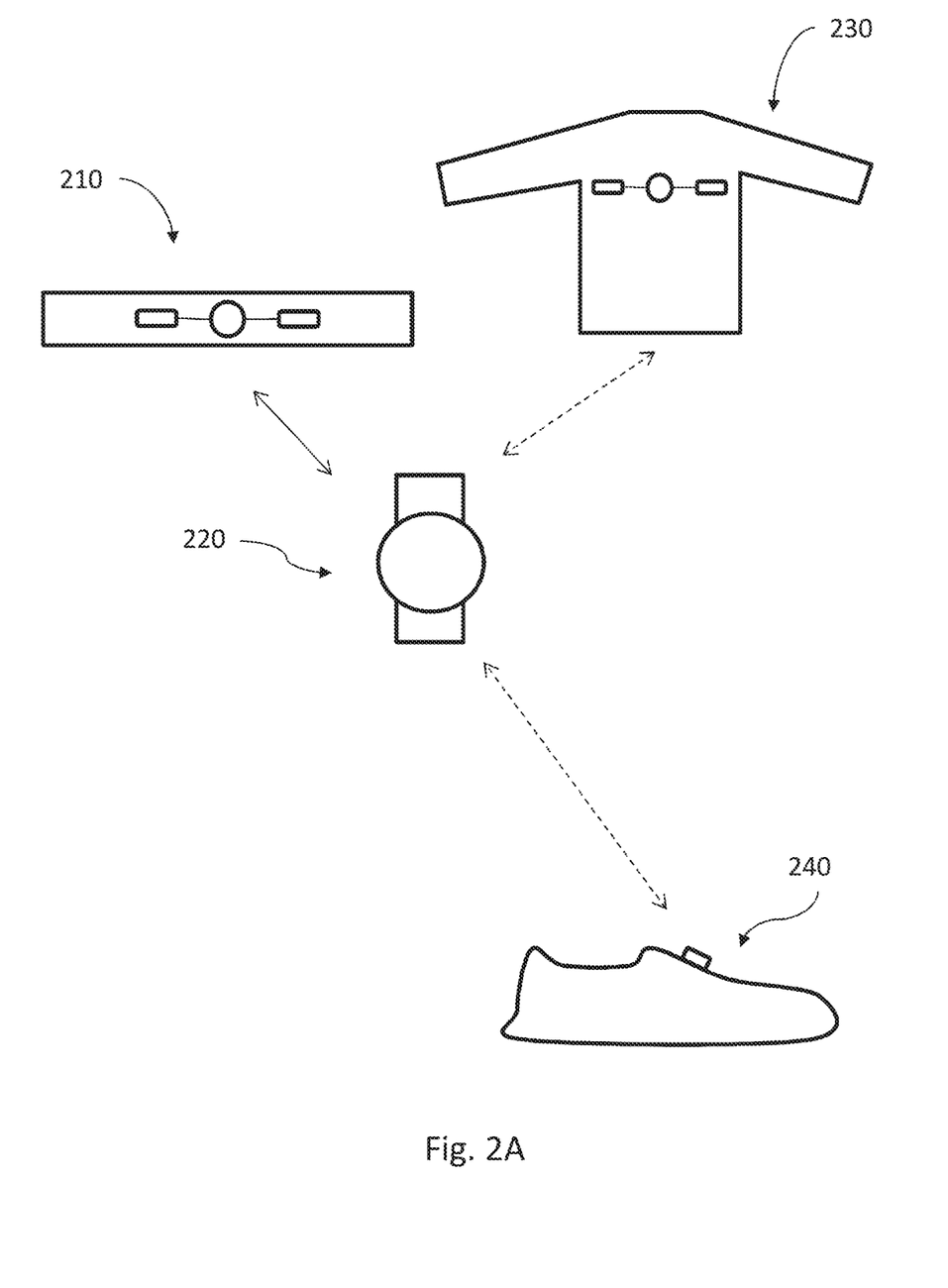
FIG. 2A shows a heartbeat measurement system according to one embodiment of the invention.

FIG. 2A shows a system with a wearable computer 220 as a data storage and/or visualization device and a heart rate belt 210 as a data-collecting device. The heart rate belt comprises an ECG sensor and an electronic module that reads and pre-processes the signal provided by the ECG sensor to at least detect heartbeat events therein. An acceleration sensor and its pre-processing capacity is provided either in the heart rate belt 210 or the wearable computer 220, or both. The heart rate belt 210 is in wireless communication with the wearable computer.

Alternatively to a heart rate belt 210, a smart garment 230 can be used, providing the same functionality as the heart rate belt 210 discussed above.

In a still further embodiment, there is provided an additional unit in the system, such as a sensor unit attached to a shoe 240 of the sportsman. The additional sensor unit may comprise an acceleration sensor providing the acceleration signal and an optional pre-processor to detect acceleration events and to convert the acceleration signal in event-based form, and is in wireless communication with the heart rate belt 210 or smart garment 230 and/or the wearable computer 220 to provide the acceleration signal or data derived therefrom for further processing or use.

It should be noted that the wearable computer can be replaced with any other wearable device, such as another wearable sports tracking unit or mobile phone capable of communicating with other components of the system.

Wireless communication of data between separate devices of a multi-device equipment takes place advantage of a wireless radio-frequency transmitter-receiver or transceiver-transceiver pair. The wireless communication protocol can be one used for communication between computers, and/or between any remote sensors, such as a Bluetooth LE or the proprietary ANT+ protocol. These are using direct-sequence spread spectrum (DSSS) modulation techniques and an adaptive isochronous network configuration, respectively. Enabling descriptions of necessary hardware for various implementations for wireless links are available e.g. from the Texas Instrument®'s handbook "Wireless Connectivity" which includes IC circuits and related hardware configurations for protocols working in sub-1- and 2.4-GHz frequency bands, such as ANT™, Bluetooth®, Bluetooth® low energy, RFID/NFC, PurePath™ Wireless audio, ZigBee®, IEEE 802.15.4, ZigBee RF4CE, 6LoWPAN, Wi-Fi®.

Figure 2B:
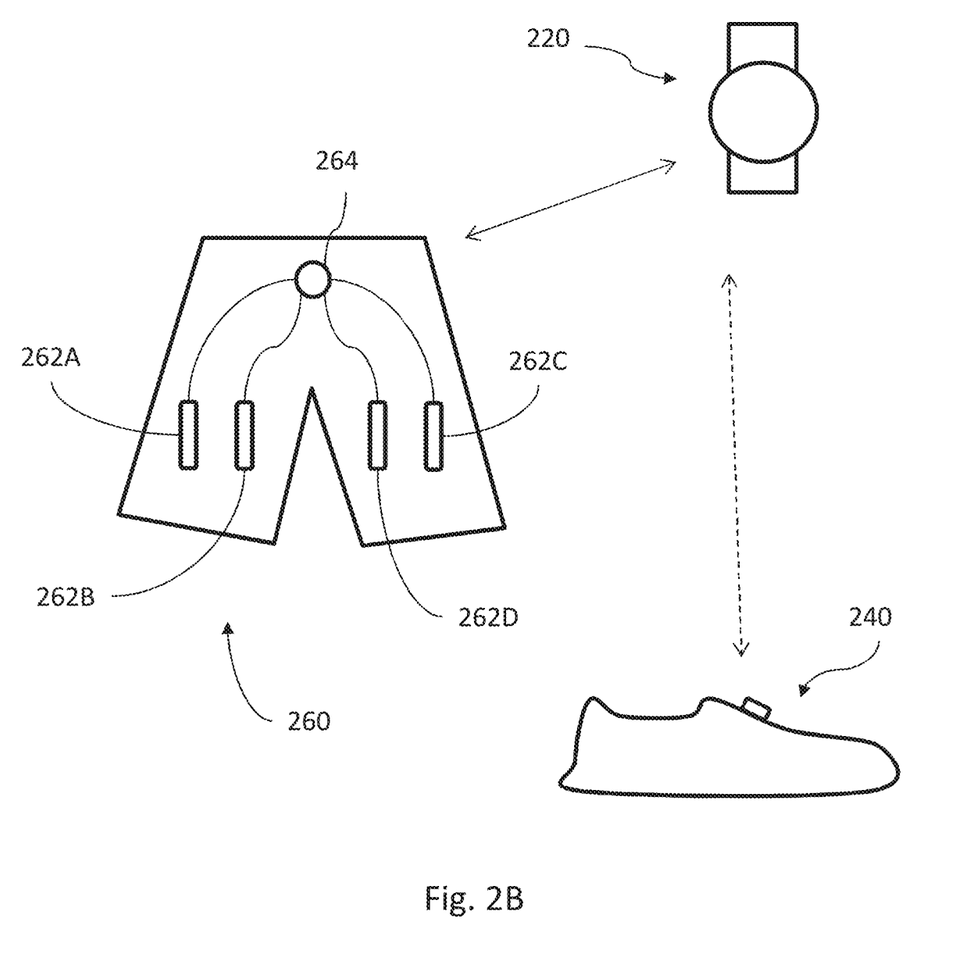
FIG. 2B shows a muscular activity measurement system according to another embodiment of the invention.

FIG. 2B shows an embodiment of the invention aimed at muscle activity monitoring, in this example leg muscle activity monitoring. It comprises basically the same components as the ECG embodiment of FIG. 2A with the ECG signal measuring item (belt 210/smart garment 230) replaced by an EMG signal measuring item 260, in this case pants equipped with EMG electrodes 262A-D connected to an EMG signal processing and communication module 264. The module 264 is capable of pre-processing the signal to find muscle activation events of a predefined kind, and forming a wireless communication link with the wearable computer 220. In this embodiment too, the acceleration sensor may be located in the module 264, wearable computer 220 or as a separate device for example attached to the 240.

Remaining computing operations necessary for the suppression of the motion-induced frequency or frequencies from the pre-processed event-based heartbeat or muscular activity signal can be carried out in the wearable computer 220 or other mobile device to which the necessary data has been transferred. If all necessary measurements are carried out by the signal measuring item 210, 230, 260, computing can be carried out in a processing unit of that item too. This provides benefits in the form of reduced battery consumption of the wearable computer (if present) and reduced data transmission between the devices.

Figure 3A:
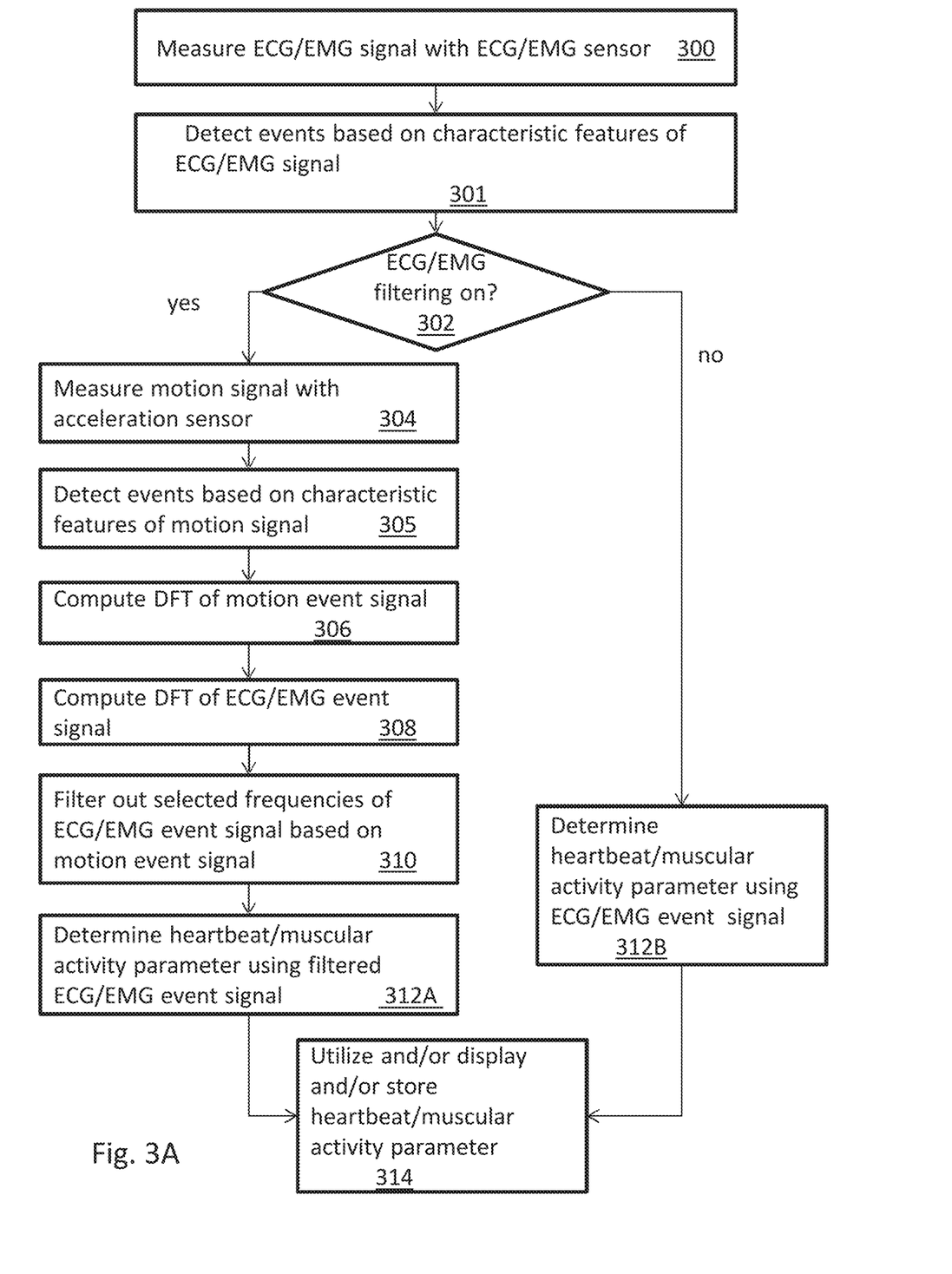
FIGS. 3A and 3B show a flow charts of the present method according to two principal embodiments of the invention, i.e. with the capability for event-based common-frequency filtering and event triggering-preventing, respectively.

FIG. 3A shows one exemplary flow schematic for present method using event-based common-frequency filtering. The heartbeat or muscular activity raw signal is measured in step 300 from a suitable location of the body of the person using a suitable sensor. In step 301, heartbeats or muscular activations are detected from the raw signal and recorded as events. A corresponding event-based time series, i.e. ECG/EMG event signal is formed accordingly. In step 302, it is checked whether rhythmic filtering feature of the system has been activated. If not, the heartbeats or muscular activities are detected in step 312B based on the raw signal using a suitable algorithm, which are known per se. If the filtering is set active, motion signal is measured in step 304 to assist in the filtering process. Motion events fulfilling predefined criteria with respect to e.g. strength of acceleration, are detected in step 305, and a corresponding motion event signal is formed. A discrete Fourier transform (DFT) of the motion event signal is computed in step 306, preferably using a suitable fast Fourier transformation algorithm. The same is carried out for the heartbeat or muscular activity signal in step 308. If the event signals are of binary form, these operations are extremely efficient as they utilize only summing operations. The DFT of the motion event signal indicates the frequencies at which there may be motion-induced artifacts present in the heartbeat or muscular activity signal. Some or all of these frequencies are then suppressed from the heartbeat or muscular activity signal, preferably in the frequency domain, to provide a filtered heartbeat or muscular activity signal in step 310. The desired heartbeat or muscular activity parameter, such as heart rate or cadence, is then determined using the filtered event signal in step 312A. In step 314, the results of the determination are then utilized in further computations to characterize the sports performance or the person and/or stored in a memory of the system and/or visualized.

According to one embodiment, the filtering is carried out in the frequency domain by subtracting the amplitude of the Fourier transformation of the motion signal from the Fourier transformation of the measured heartbeat or muscular activity signal.

Figure 3B:
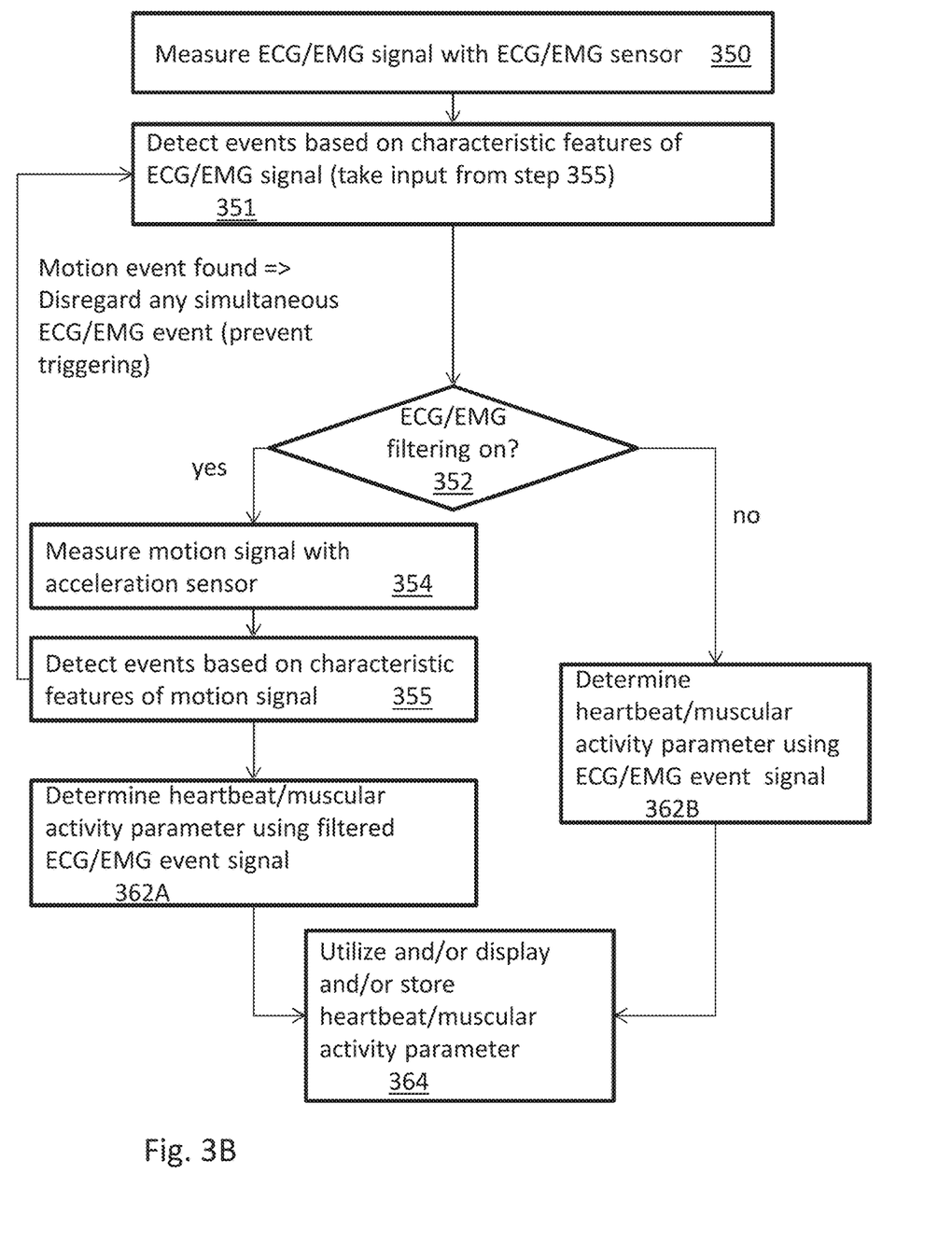

FIG. 3B illustrates the present method with motion event-based ECG/EMG event disregarding (triggering-preventing) algorithm. Again, the heartbeat or muscular activity raw signal is measured in step 350 as described above. In step 351, heartbeats or muscular activations are detected from the raw signal and recorded as events (the detection algorithm however now taking input from step 355 explained below in order to disregard some of the potential ECG/EMG events if there is too significant motion interference). A corresponding event-based time series, i.e. ECG/EMG event signal is formed accordingly.

In step 352, it is checked whether the event-triggering-preventing filtering feature of the system has been activated. If not, the heartbeats or muscular activities are detected in step 352B as above. If the filtering is set active, motion signal is measured in step 354 to assist in the filtering process. Motion events fulfilling predefined criteria with respect to e.g. strength of acceleration, are detected in step 355 and information on such events is sent as input to step 351, where the simultaneousness of motion event causes a potential ECG/EMG event not to be recorded in the ECG/EMG event signal. The desired heartbeat or muscular activity parameter, such as heart rate or cadence, is then determined using the filtered event signal in step 362A and used/displayed/stored in step 364. For displaying, there may be provided a display in a device unit part of the equipment. Storage preferably takes place in a memory element in a device unit part of the equipment or a separate unit in wireless communication with the equipment.

Using the method of FIG. 3B, the filtering can be carried out by completely ignoring periods of the heartbeat or muscular activity signal that take place during periods of high acceleration. In other words, during acceleration peaks, the processing unit need not carry out heartbeat or muscular activity detection or at least disregard any events potentially detected. There may, for example, be provided a threshold acceleration level above which heartbeat or muscular activity is not being detected or detected activities are rejected as being potentially contributed by the acceleration. This results in an incomplete series of heartbeats, but the heartbeats in this series being correct with higher probability than those without this kind of filtering. Then, using a statistical method, one can deduct the average heartbeat interval and therefore the heart rate. For example, if heartbeats are detected from the filtered signal at average intervals $T_1$, $T_2=2T_1$ (and potentially $T_3=3T_1$ etc. . . . ), it can be concluded that the heartbeat interval is $T_1$ (and $T_2$, $T_3$ etc. are due to heartbeats "skipped" because of high acceleration). A Discrete Fourier Transform is again a useful statistical tool to find the heartbeat interval, because it is unsensitive to occasionally missing heartbeat events and thus is able to find the basic heart rate frequency.

The steps of the FIGS. 3A and 3B can naturally take place in any suitable order, which may deviate from the one illustrated. Moreover, if the present signal cleaning method is set to take place by default, steps 302/352 and 312B/362B are not needed.

Typical further uses of the heartbeat parameter include energy consumption estimation and training effect estimation. Muscular activity parameter can be used for example for detailed physical training analysis and performance optimization.

In one preferred embodiment, the event signals referred to above are in binary form, i.e. comprising only a series of zeros and ones, the location of the values in the binary stream corresponding to the moments of time of the detected events.

Figure 4A:
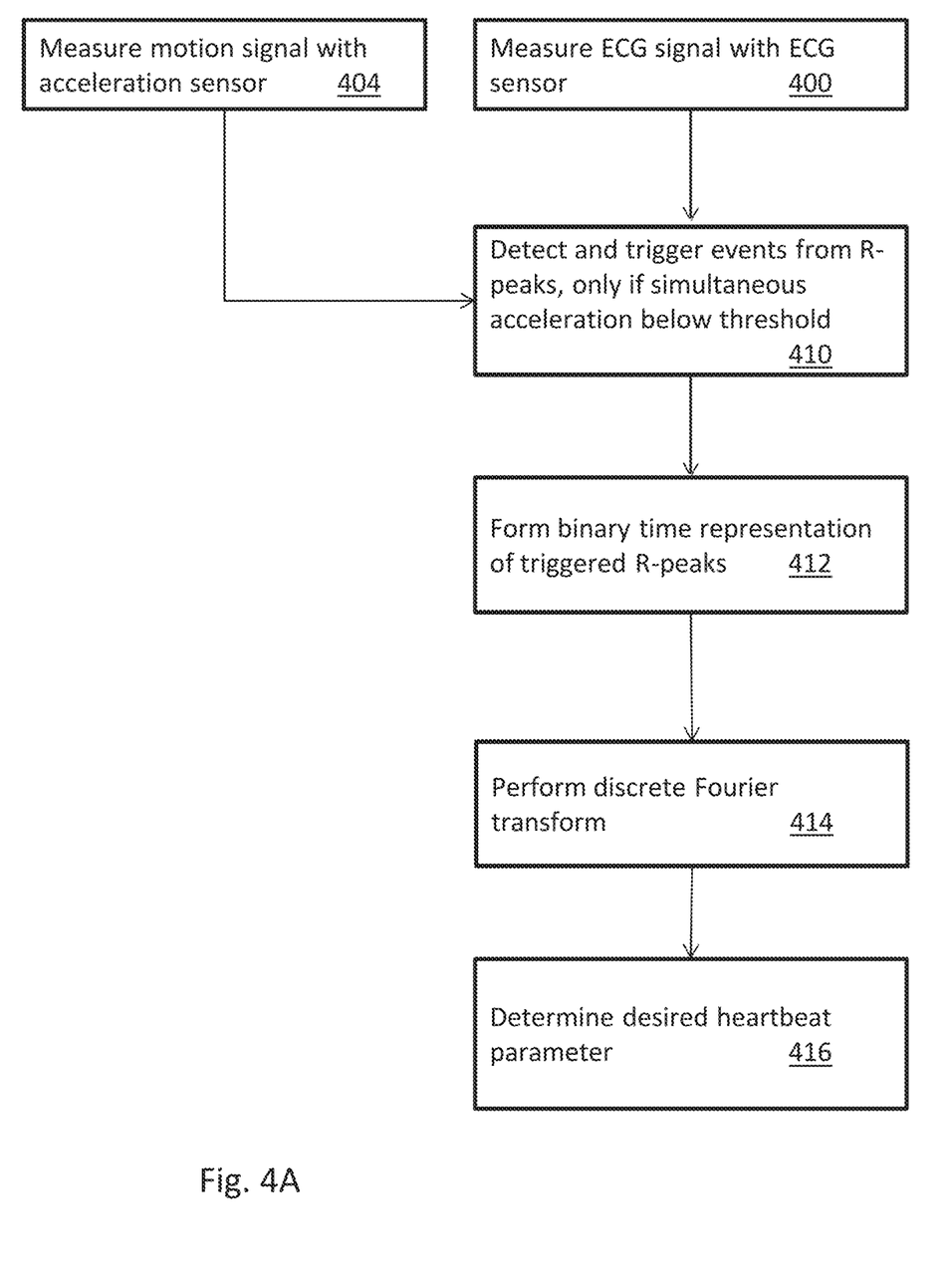
FIGS. 4A and 4B show more detailed flow charts of the present method simplified to heartbeat measurement, according to the principal embodiments of the invention.

FIG. 4A shows a flow chart of exemplary embodiment utilizing event triggering-preventing in the case of heartbeat measurement. The method starts by measuring ECG signal and motion signal in steps 400 and 404, respectively. In step 410, the ECG signal is analyzed to as to detect R-peaks in the electronic QRS-complexes detected by the heartbeat sensor. Besides the ECG signal, the motion signal is taken as input to the detection algorithm. An R-peak is set to trigger a heartbeat event only if there are no significant events in the motion signal. By significant event is typically meant that the acceleration stays below a predefined threshold level. The passed heartbeat events are represented as a binary time series for example with "1" representing a heartbeat event at a predefined point of time and "0" representing non-existence of a heartbeat event, in step 412. In optional step 414, the binary series is Fourier-transformed using a binary DFT algorithm. In one embodiment, step 414 is performed only if there is significant amount of noise in the binary series, detected by time-domain statistics. Using the time series or its frequency-domain representation, the desired heartbeat parameter can be determined.

Figure 4B:
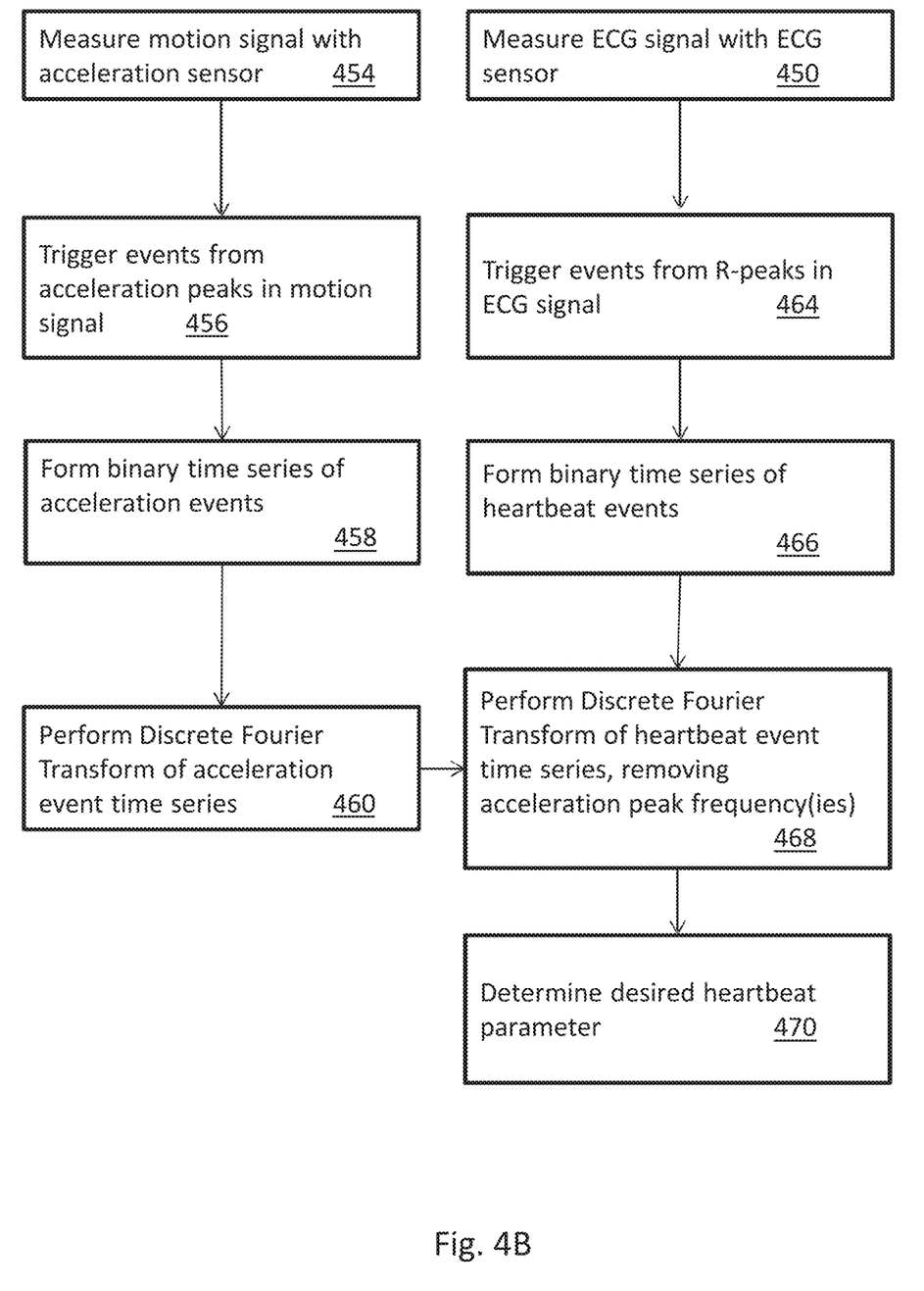

FIG. 4B shows in detail an exemplary common-frequency filtering embodiment for heartbeat measurement. The method again comprises simultaneously measuring the ECG signal and motion signal in steps 450 and 454. From both signals, relevant features, typically R-peaks and acceleration peaks, respectively, are detected and events triggered in the case of positive findings, in steps 464 and 456. The events are formed as binary time series in both cases in steps 466 and 458. The heartbeat and acceleration event binary series are Fourier-transformed using a binary DFT algorithm in steps 460 and 468. The Fourier-transformation of the acceleration series is used to remove a frequency or many frequencies that are common in both series. As a result, a purified heartbeat event signal is obtained, which can be used to determine the desired heartbeat parameter in step 470.

It should be noted that the signal filtering according to the invention needs not be turned on for the whole time. It may for example be used only in the beginning of an exercise for a predefined period of time, when the motion artifacts discussed above are most significant.

There are several Discrete Fourier Transform algorithms available in the literature that can be used in connection with the invention. The time span of even time series that the DFT algorithm "sees" can be suitably adjusted.

Figure 5A:
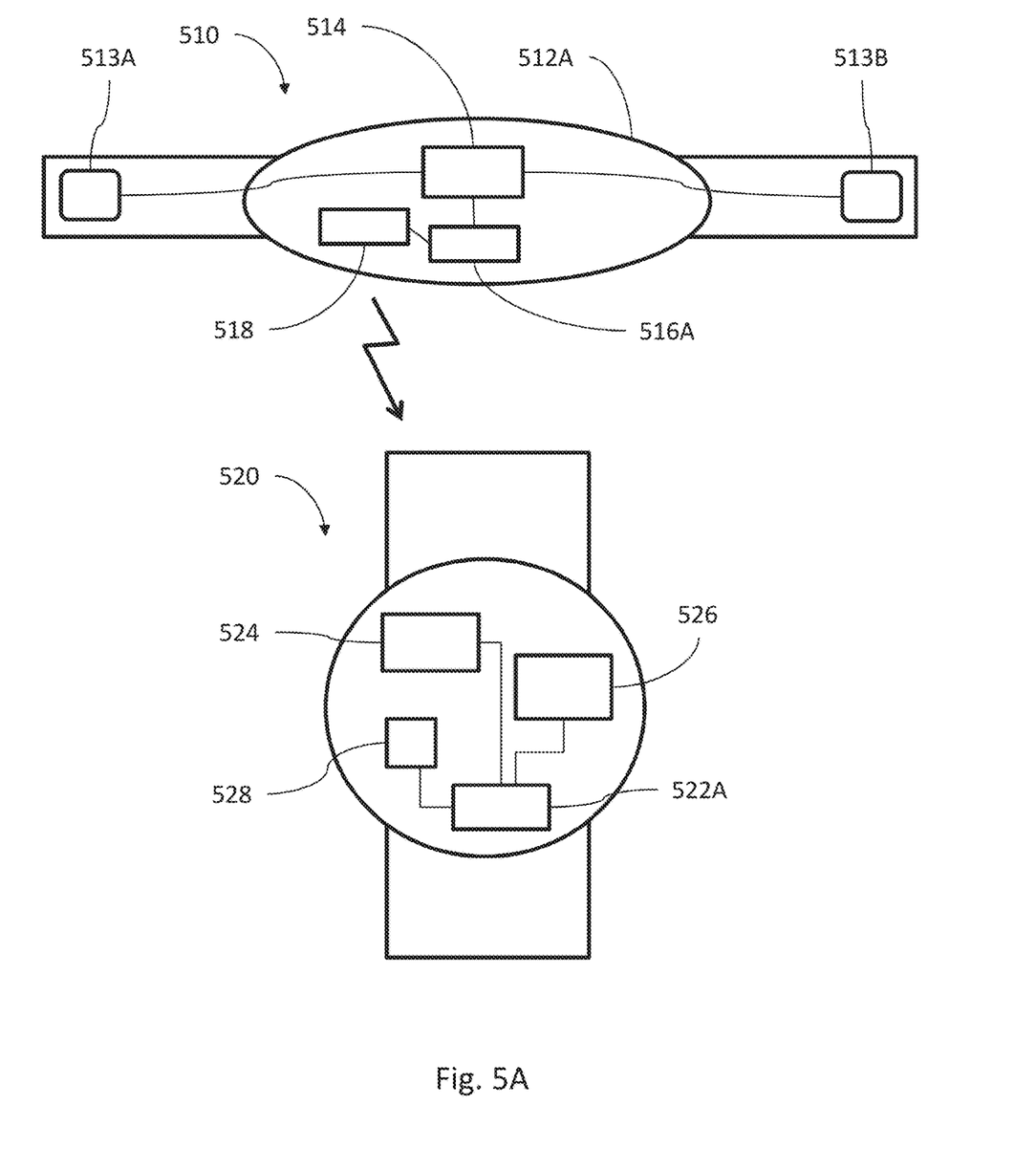
FIGS. 5A and 5B show exemplary systems, which can be used to implement the invention.

FIG. 5A depicts one potential implementation of the system in more detail. There is provided a heart rate belt 510 with a pair of ECG electrodes 513A, 513B connected to an ECG signal pre-processor 514 (typically including at least an A/D converter) contained in an integral or removable electronics module 512A. The heartbeat signal is wirelessly communicated to a wearable computer 520 via a radio transmitter unit 518 in the belt 510 and radio receiver unit 524 in the wearable computer. The receiver unit 524 is functionally connected to a processing unit 522A. In addition, there is provided an acceleration sensor 528 in the wearable computer functionally connected to the processing unit 522A.

The processing unit 522A is configured to perform the filtering actions on the heartbeat signal provided by the heart rate belt 510 based on the acceleration signal provided by the acceleration sensor 528. The processing unit 522A is also adapted to detect individual heartbeats from the filtered signal and typically also further computations using the heartbeat data.

The system of FIG. 5A is useable but it has to be taken into account that the acceleration data does not directly correspond with the motion of the ECG sensor. However, since the motion of the hand correlates with the motion of the chest during running, for example, the acceleration measured this way can be used for the purposes of the invention.

Figure 5B:
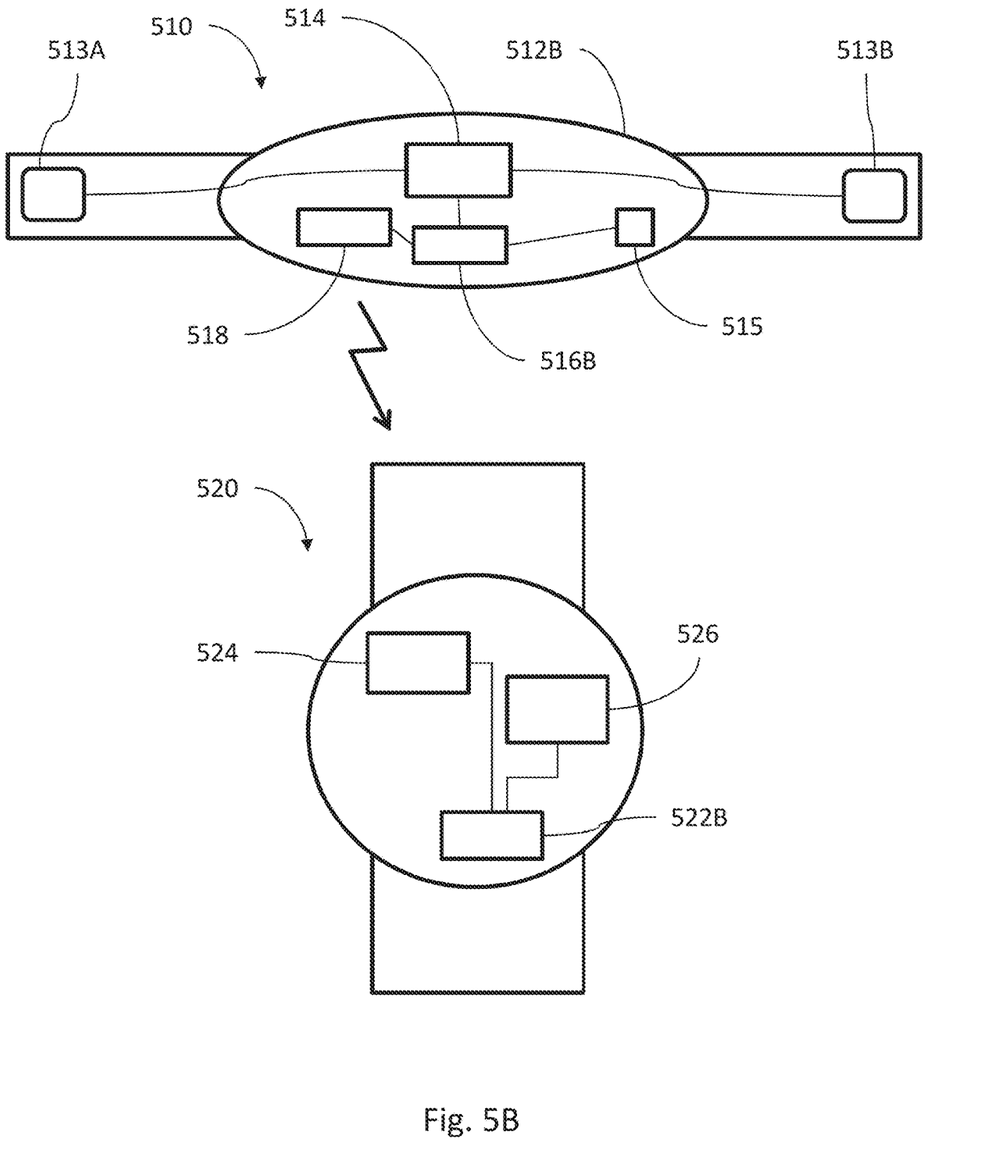

FIG. 5B shows an embodiment mostly similar to that of FIG. 5A but having an acceleration sensor 515 in the electronics module 512B of the heart rate belt. This way the acceleration signal directly corresponds with the motion of the heart rate belt and this gives better information for filtering purposes than the system of FIG. 5A. The processing unit 516B is configured to read the acceleration signal from the acceleration sensor 515 and to perform the filtering operations described above directly in the heart rate belt.

It is to be understood that the embodiments of the invention disclosed are not limited to the particular process steps, units, components, devices, materials or products disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, various embodiments and examples of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the description, numerous specific details are provided, such as examples of shapes and dimensions etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. Wearable electronic equipment for determining a heartbeat or muscular activity parameter of a person during a physical performance, comprising:
   a heartbeat or muscular activity sensor configured to provide a heartbeat or muscular activity signal, respectively;
   a motion sensor configured to provide a motion signal corresponding to movement of the person; and
   a processing unit configured to:
   detect during said physical performance from the heartbeat or muscular activity signal first events corresponding to characteristic features of individual heartbeats or muscle activations, respectively, and to record a first series of said first events during a time span in said physical performance,
   detect during said physical performance from the motion signal acceleration events which are stronger above a predefined threshold as second events, and to record a second series of said second events during said time span in said physical performance,
   generate an incomplete series of heartbeats by selectively removing, during said physical performance, such first events from said first series of events in said time span which coincides with a second event in said second series of events, and determine a heart rate of the person based on the incomplete series of heartbeats.

2. The wearable electronic equipment according to claim 1, wherein the processing unit is further configured to disregard periods of the heartbeat or muscular activity signal that coincide with second events when recording said first series of events.

3. The wearable electronic equipment according to claim 1, wherein the processing unit is further configured to:
record said first series of said first events detected as a binary series, where one binary value represents detected events and the opposite binary value represents a non-existence of such events,
record said second series of said second events detected as a binary series, where one binary value represents detected events and the other binary value represents a non-existence of such events, and
filter frequency components of said first series of events that are in common with at least one frequency component of the second series of events, in order to form a filtered first series of events.

4. The wearable electronic equipment according to claim 3, wherein the processing unit is further configured to carry out filtering of frequency components by:
performing a Discrete Fourier Transform (DFT) of said first binary series,
performing a Discrete Fourier Transform (DFT) of said second binary series, and
filtering common frequency components of the first and second binary series from said first series of events.

5. The wearable electronic equipment according to claim 1, wherein the motion sensor is an acceleration sensor.

6. The wearable electronic equipment according to claim 1, wherein the wearable electronic equipment is configured to determine a muscular activity parameter and the muscular activity parameter includes cadence and/or one or more parameters derived therefrom.

7. The wearable electronic equipment according to claim 1, wherein the one or more heartbeat or muscular activity sensors and the motion sensor are located in a single device unit.

8. The wearable electronic equipment according to claim 7, wherein the single device unit further comprises at least part of said processing unit.

9. The wearable electronic equipment according to claim 1, wherein the processing unit is located in a different device unit than the heartbeat or muscular activity sensor and/or the motion sensor.

10. The wearable electronic equipment according to claim 1, wherein the heartbeat or muscular activity sensor comprises electric ECG or EMG electrodes, respectively.

11. The wearable electronic equipment according to claim 10, wherein the ECG or EMG electrodes are connected to a measurement circuit with input impedance of less than 50 kOhm.

12. The wearable electronic equipment according to claim 10, wherein the ECG or EMG electrodes are laminated onto a fabric structure.

13. The wearable electronic equipment according to claim 1, wherein the heartbeat or muscular activity sensor includes an optical sensor, pressure sensor or acceleration sensor.

14. The wearable electronic equipment according to claim 1, further comprising a wireless communication unit in a first device unit comprising said heartbeat or muscular activity sensor and a first part of the processing unit, the first part of the processing unit being further configured to communicate said first events to a second device unit containing a second part of the processing unit through said wireless communication unit.

15. The wearable electronic equipment according to claim 1, wherein the processing unit is further configured to remove such first events from said first series of events in said time span which occur at the same frequency of a second event in said second series of events.

16. A method of monitoring a physical performance of a person comprising:
measuring a heartbeat or muscular activity signal using a measurement device being at least partly positioned against the skin of the person;
measuring movement of at least one part of the measurement device using a motion sensor for providing a motion signal;
detecting during said physical performance from the heartbeat or muscular activity signal first events corresponding to characteristic features of individual heartbeats or muscle activations, respectively and recording a first series of said first events during a time span in said physical performance;
detecting during said physical performance from the motion signal acceleration events which are above a predefined threshold as second events, and recording a second series of said second events during said time span in said physical performance;
generating an incomplete series of heartbeats by selectively removing during said physical performance such first events from said first series of events in said time span which coincides with a second event in said second series of events; and
determining a heart rate of the person based on the incomplete series of heartbeats.

17. The method according to claim 16, further comprising the step of disregarding periods of the heartbeat or muscular activity signal that coincide with second events when recording said first series of events.

18. The method according to claim 16, further comprising the steps of:
recording said first series of said first events as a binary series, where one binary value represents detected events and the opposite binary value a non-existence of such events,
recording said second series of said second events detected as a binary series, where one binary value represents detected events and the opposite binary value a non-existence of such events, and
filtering frequency components of said first series of events that are in common with at least one frequency component of the second series of events, in order to form a filtered first series of events.

19. The method according to claim 18, further comprising:
performing a Discrete Fourier Transform (DFT) of said first binary series,
performing a Discrete Fourier Transform (DFT) of said second binary series, and
filtering common frequency components of the first and second binary series from said first series of events.

* * * * *